US012779251B2

(12) United States Patent
Griffin et al.

(10) Patent No.: US 12,779,251 B2
(45) Date of Patent: Nov. 3, 2026

(54) STANDOFFS FOR TARGETED ULTRASOUND THERAPY

(71) Applicant: GE Precision Healthcare LLC, Waukesha, WI (US)

(72) Inventors: Weston Blaine Griffin, Niskayuna, NY (US); David Andrew Shoudy, Niskayuna, NY (US); Warren Lee, Niskayuna, NY (US); Craig Patrick Galligan, Averill Park, NY (US); Andrew A. Burns, Schenectady, NY (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

(21) Appl. No.: 18/808,842

(22) Filed: Aug. 19, 2024

(65) Prior Publication Data

US 2026/0048278 A1 Feb. 19, 2026

(51) Int. Cl.
*A61N 7/00* (2006.01)
*C08J 3/075* (2006.01)

(52) U.S. Cl.
CPC ................ *A61N 7/00* (2013.01); *C08J 3/075* (2013.01); *A61N 2007/0026* (2013.01)

(58) Field of Classification Search
CPC ........................................................ A61N 7/00
See application file for complete search history.

(56) References Cited

U.S. PATENT DOCUMENTS

| | | | | |
|---|---|---|---|---|
| 5,265,614 A | | 11/1993 | Hayakawa | |
| 6,719,699 B2 | * | 4/2004 | Smith | A61B 8/4281 600/459 |
| D629,527 S | * | 12/2010 | Crunkilton | D24/187 |
| D724,745 S | * | 3/2015 | Orome | D24/186 |
| 10,022,147 B2 | * | 7/2018 | Lee | A61B 8/4455 |
| 10,064,599 B2 | * | 9/2018 | Desai | A61B 8/4422 |
| 10,603,521 B2 | * | 3/2020 | Emery | A61N 7/02 |
| 10,820,885 B2 | * | 11/2020 | Cohen | A61B 8/5292 |
| 11,957,511 B2 | * | 4/2024 | Cermak | A61B 8/4281 |
| 2005/0096547 A1 | * | 5/2005 | Wendelken | A61B 8/4281 600/459 |
| 2005/0240102 A1 | * | 10/2005 | Rachlin | A61B 8/10 600/459 |
| 2006/0058705 A1 | * | 3/2006 | Leonetti | A61B 17/2251 601/1 |

(Continued)

FOREIGN PATENT DOCUMENTS

WO WO-2026017314 A1 * 1/2026 ........... G10K 15/043

OTHER PUBLICATIONS

Aquaflex(R) website for device, via wayback machine for May 2023 (Year: 2023).*

(Continued)

*Primary Examiner* — Joanne M Rodden
(74) *Attorney, Agent, or Firm* — Fletcher Yoder, P.C.

(57) ABSTRACT

Embodiments of the present disclosure relate to a gel standoff for use with an ultrasound probe and compositions and techniques for making and using the same. The composition and properties of the gel standoff may be customized to accommodate a subject's clinical needs and/or a treatment protocol that utilizes the ultrasound probe. In certain embodiments the gel standoff may be designed to treat a subject via neuromodulation.

21 Claims, 14 Drawing Sheets

(56) References Cited

U.S. PATENT DOCUMENTS

2009/0177083 A1* 7/2009 Matsumura ............. B06B 1/067 600/437
2010/0081893 A1 4/2010 Jarvik et al.
2010/0113984 A1* 5/2010 Leonetti ............. A61B 17/2251 601/2
2010/0185097 A1* 7/2010 Hall ................... A61B 17/2251 600/459
2011/0087107 A1* 4/2011 Lindekugel .......... A61B 8/4455 600/459
2011/0313293 A1* 12/2011 Lindekugel ............ A61B 10/00 600/459
2013/0085391 A1* 4/2013 Matsumura .......... A61B 8/4411 600/443
2013/0116571 A1* 5/2013 Cox ..................... A61B 8/4281 600/472
2013/0338503 A1* 12/2013 Cohen .................. A61B 8/4411 600/443
2014/0180116 A1* 6/2014 Lindekugel .......... A61B 8/4455 600/459
2014/0206976 A1* 7/2014 Thompson ........... A61B 5/6833 600/391
2020/0245971 A1 8/2020 Lindekugel
2022/0233886 A1* 7/2022 Shoudy .................... A61N 7/00
2023/0380803 A1 11/2023 Jiang
2024/0173574 A1 5/2024 Kaplan
2024/0382175 A1* 11/2024 Staebler ............... A61B 8/4272

OTHER PUBLICATIONS

Liu G, Ding Z, Yuan Q, Xie H, Gu Z. Multi-Layered Hydrogels for Biomedical Applications. Front Chem. Sep. 25, 2018;6:439. doi: 10.3389/fchem.2018.00439. PMID: 30320070; PMCID: PMC6167445. (Year: 2018).*
EP application 25191886.8 filed Jul. 25, 2025—extended Search Report issued Jan. 7, 2026; 10 pages.

* cited by examiner

STANDOFFS FOR TARGETED ULTRASOUND THERAPY

FIELD OF THE TECHNOLOGY DISCLOSED

The subject matter disclosed herein relates to identifying, targeting and/or dosing regions of interest in a subject via application of energy (e.g., neuromodulating ultrasound energy), such as to cause targeted physiological outcomes. In particular, the disclosed techniques may be useful in facilitating the accurate delivery of a therapeutic dose of ultrasound energy to a targeted region.

BACKGROUND

Ultrasound-based neuromodulation has been used to treat a variety of clinical conditions. However, the targeting of specific tissue for neuromodulation may be challenging. Certain patients may have variations in organ size or location relative to other patients based on their height, weight, age, gender, clinical condition, and so forth, which may impact targeting and dose delivery when using various neuromodulation techniques.

In the context of neuromodulation using ultrasonic devices, other common challenges with delivering accurate ultrasonic therapy at a prescribed dose include poor acoustic coupling between the therapy probe and the patient, "lift off" of a portion of the probe from the patient, poor image quality, or presence of an acoustic reflector or absorber (e.g., bone structures, such as ribs, bowel gas, and so forth) in the therapy beam path. Such factors can result in delivery of an inaccurate dose amount and/or lead to patient discomfort.

BRIEF DESCRIPTION

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

In one embodiment, a gel standoff is provided. In accordance with this embodiment, the gel standoff comprises a gel standoff body comprising a moldable material. The gel standoff also comprises one or more mating features formed within the gel standoff body. The one or more mating features are configured to conform to one or more structural features of an ultrasound probe. The gel standoff further comprises a patient-facing surface. The patient-facing surface is configured to contact skin of a patient when in use.

In one embodiment, a method of mounting a gel standoff to an ultrasound probe is provided. In accordance with this method, a lid of a gel pad pack is removed. The gel standoff is exposed in the gel pad pack when opened. The gel pad pack is aligned with an ultrasound probe. One or more mating features of the gel standoff are aligned with complementary mating features of the ultrasound probe when aligned. The gel standoff in the gel pad pack is pressed to the ultrasound probe. The gel standoff pulls away from the gel pad pack and engages with the ultrasound probe in response to the pressing. The ultrasound probe with the engaged gel standoff is separated from the gel pad pack.

In one embodiment, a method of using a gel standoff is provided. In accordance with this method, the gel standoff is inserted into a complementary cavity of an ultrasound probe. The ultrasound probe is pressed against a subject. Energy is applied through the gel standoff toward a region of interest in the subject to cause neuromodulation. The gel standoff is removed from the ultrasound probe after the energy application is complete.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
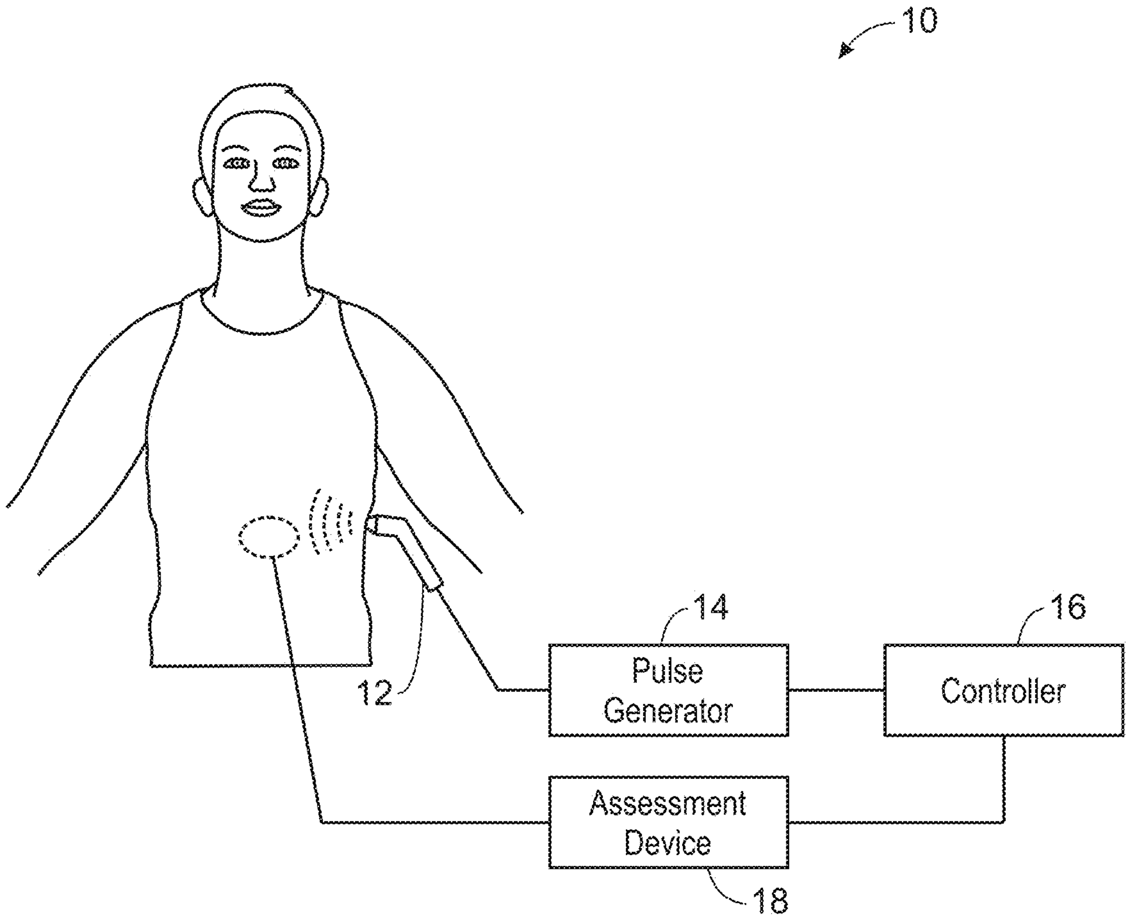
FIG. 1 is a schematic representation of a neuromodulation system according to embodiments of the disclosure.

One or more specific embodiments are described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to, "for example", "for instance", "such as", "e.g.", "including", "in certain embodiments", "in some embodiments", and "in one (an) embodiment." All numerical values within the detailed description herein are modified by "about" the indicated value, and take into account experimental error and variations that would be expected by a person having ordinary skill in the art. For example, "about" or "approximately" may refer to ±0.5%, ±1%, ±2, ±5%, ±10%, or ±15%.

When introducing elements of various embodiments of the present disclosure, the articles "a", "an", "the", and "said" are intended to mean that there are one or more of the elements. The terms "comprising", "including", and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The term "gel standoff" (e.g., a hydrogel standoff) is used herein to describe a non-liquid, non-gaseous standoff that may be conformable or moldable to fit within the internal cavity of an ultrasound probe and/or conform to a patient's skin. Furthermore, it should be noted that the composition of the "gel standoff" is not limited to gel. Accordingly, as described herein, "gel" may refer to hydrogels, waxes, polymers, solid oils, and other moldable and/or conformable materials.

Ultrasound-based neuromodulation has been used to treat a variety of clinical conditions, including metabolic disorders, such as diabetes or hyperglycemia, inflammation or immune disorders, and so forth. In practice, ultrasound-based neuromodulation may be implemented as image-guided ultrasound therapy, and such applications may utilize various transducer imaging/therapy configurations. For example, an ultrasound probe may include a central imaging transducer and a separate outer ring therapy transducer. Such a configuration is often used for high-intensity focused ultrasound (HIFU) therapy but is also relevant for neuromodulation when utilizing higher power levels than conventional imaging. The separate imaging and therapy transducers are optimized for their respective purpose and often interleaved vs. time by using the imaging transducer to localize an internal anatomical target and subsequently using (i.e., switching to) the therapy transducer to deliver an ultrasonic dose to the target. In most situations, the imaging transducer and therapy transducer are co-centric or otherwise adjacently attached with separate lenses or a co-molded lens (or a fluid filled cap) over both transducers, and standard ultrasound coupling gel may be used in conjunction. For example, an adjacently attached transducer configuration may use a therapy transducer with concave geometry that utilizes ultrasound coupling gel to fill the concave cavity during application, resulting in a messy application and overall poor user experience. Additionally, this arrangement does not typically enable determining if a "clear path" is present for the therapy beam to propagate from an ultrasound probe to a target region and beyond. In general, determining such a clear path for the therapy beam relies on various factors (e.g., an absence of bone or bone-like structures, presence or absence of gas-filled pockets or cavities, good acoustic coupling, no "lift off" of the probe head from the patient surface) and is useful in providing accurate dosing and patient safety. As such, while certain fluid-filled cap configurations and geometries may help to enable clear path determination, they may have the unintended consequence of degrading image quality.

For example, one issue that can arise in using image-based techniques to evaluate or guide the application of ultrasonic therapy energy to a target region within a patient (such as for the purposes of neuromodulation) is "blind spots," which corresponds to regions of the patient that are traversed by the therapy beam but not observed (e.g., seen) with the imaging technique. As used herein, the path of the therapy beam (i.e., the therapy beam path) encompasses areas "from-to-beyond" the target region (i.e., from the transducer to the target region and beyond the target region) in addition to objects or structures near the target region. For practical purposes, the therapy beam may be envisioned as a cone that converges from the transducer to the target region and another cone that diverges from the target region to beyond. With respect to blind spots traversed by the therapy beam along this path but not imaged by the imaging beam, these blind spots may lead to the therapy modulating "off target" (i.e., affecting or applying energy to patient regions that are not part of the target region) and/or failing to deliver the prescribed dose to the patient. By way of example, for a centered imaging array and outlying therapy array(s) that are applied close to or adjacent the patient skin, patient areas near the skin line may be unobserved by the imaging array but traversed by the therapy beam. Such blind spots may therefore be problematic in an image-guided therapy context.

Relatedly, additional challenges with delivering accurate and safe ultrasonic therapy using image-guided techniques may include poor acoustic coupling between the treatment device and patient, "lift off" of a portion of the treatment device relative to the patient, and the presence of an acoustic reflector or absorber (e.g., bone structures such as ribs, gas-filled pockets or regions, such as bowel gas) in the therapy beam path. With respect to these factors, poor acoustic coupling may manifest as an overly blurry or dim image, though not necessarily at an edge of the image, which may be more indicative of a "lift off" event. Partial "lift off" may be indicated by no image or a dim image along an edge of the image and may result in therapy transducer heating and reduced dose delivery. Acoustic reflection or absorption (e.g., "shadowing") may occur when the transducer(s) are over the shadow-causing structure (e.g., ribs). Such factors can result in delivery of an inaccurate dose, present a safety hazard (e.g., burn, cavitation) to the patient, and/or cause patient discomfort.

Importantly, the ultrasound pressure wave creates a mechanical force that is applied to the internal tissues. If the mechanical force becomes too great, this can lead to undesired mechanical bioeffects. The ultrasound beam can also cause internal tissues to heat up while the tissue absorbs the ultrasound energy, as factors such as increased power or effective duty cycle may cause increased internal heating. If the internal heating is too large, a number of undesired thermal bioeffects may occur. In addition, tissue attenuation and acoustic impedance vary across different tissue types. For example, bone attenuation and impedance are ~15× and ~5× greater, respectively, than the next highest internal soft tissue. Much of the focus around ultrasound safety with bones results from this extreme difference, where the high attenuation can result in heating of the bone, and the high difference in acoustic impedance creates strong reflections at tissue/bone interfaces that can result in defocusing or redirecting the acoustic energy. Additionally, internal gas structures, when excited with a high mechanical force, may cavitate, which may affect surrounding tissues.

Due to the issues noted above, as well as the need to ensure accurate dose delivery (and thus effective therapy), it may be desirable to be able to steer and/or focus the ultrasound beam(s) without having to reposition or reorient the probe head contacting the patient. Further, the contact between the probe head and patient should be conducive to propagation of the ultrasound beam as well as to mechanical and/or electronic steering and focusing techniques. Accordingly, determining a path adjustment and/or an analysis of a path may encompass a multitude of factors (e.g., an absence of bone or otherwise dense, acoustically reflective structures, an absence of gas filled cavities, an absence of other anatomies that are undesirable for receiving a portion of the ultrasonic energy, good acoustic coupling, no "lift off" of the probe interface, and so forth), some of which may be considered in a given path determination. The types of factor(s) that are considered may depend on considerations such as the therapy protocol, the patient anatomy, the system geometry, the prescribed frequencies and/or dose, and so forth.

With this in mind, the techniques and approaches discussed herein comprise combinations of physical embodiments and implementations that may be employed to provide for the safe and accurate delivery of the ultrasound therapy to the target. While the presently described techniques and approaches may be useful to a trained technologist administering an ultrasonic therapy treatment to a target region of a patient, these techniques and approaches may also be employed to allow a medically untrained individual, including the patient themselves, to safely administer an ultrasonic therapy treatment without risk of injury and while achieving the desired medical effect.

Provided herein are gel pad standoffs (e.g., gel pads, gel pad inserts, gel standoffs) that are designed for use with multiple transducer designs (e.g., one-transducer, two-transducers, three-transducers, or more) ultrasound therapy configurations to ensure clear path for therapy delivery and high image quality in imaging or targeting contexts with simple user workflow considerations and minimal to no clean up post-procedure. The gel standoffs help to ensure patient safety for ultrasound therapy procedures by minimizing and/or eliminating poor coupling, lift off, and/or facilitating mechanical or electronic steering (such as to avoid or work around acoustic reflectors or absorbers (i.e., bone/ribs, bowel gas) in the therapy beam path). Accordingly, the gel standoff is configured to allow acoustic energy to pass through from the transducers of an ultrasound probe to a contacted patient surface to provide a therapeutic effect and/or for imaging. The gel standoffs described herein exhibit substantial advantages over the commonly-employed hard-shell fluid-filled caps. For example, using gel standoffs provides a significant improvement in image quality relative to fluid-filled caps (e.g., acoustic impedance matching is better achieved relative to hard-shell caps, reducing reverberations), removes the need for internal oil/liquid, thereby simplifying overall probe design, reduces costs, and removes the need for ultrasound gel for improved patient experience/workflow.

Additional features are presented that specifically tailor the gel pad geometry to match or conform to patient-specific geometries. For example, the gel standoff geometry can be custom molded to fit an internal cavity of a two-transducer ultrasound probe geometry for acoustic coupling. The gel pad may, in some embodiment, exhibit snap-in features (e.g., grooves and corresponding ridge on probe), enabling hands-free press insertion. In some embodiments, the geometry of the gel standoff may be modified to conform to patient body shape at a probe placement location (e.g., region of interest). In this way, the gel standoff may be custom fit to specific patients or use cases (e.g., an anatomical structure (i.e., a region of interest) to be targeted, depth of the target), thereby increasing comfort, stability, and acoustic coupling.

Furthermore, the gel standoff may be tailored to have a material composition with specific acoustic properties to enable a more effective therapy delivery. For example, the gel standoff may be tailored or constructed to have a specific material composition or combination of compositions, such as a multi-material composition. In some embodiments, a multi-material composition may include a lens-like structure embedded or otherwise formed within the gel standoff to angulate the ultrasound beam toward a region of interest. Additionally, the material composition of the gel standoff may be selected or tailored to change attenuation of the medium or sound velocity or acoustic impedance to achieve desirable beam properties, enhance coupling, exhibit "wetness" for long-term use, or assist in focusing the therapy beam on the target. For example, attenuation at about 5 decibels/centimeter/megahertz (dB/cm/MHz) may be undesired in certain contexts (e.g., bone attenuation is about 3.54 dB/cm/MHz). As such, the gel standoff may have attenuation of less than or equal to 0.1 dB/cm/MHz in certain embodiments. In other embodiments, the gel standoff may be configured with an attenuation between 0.1 dB/cm/MHz and 5 dB/cm/MHz to approximate a tissue attenuation. Similarly, in certain embodiments the acoustic impedance of the gel standoff may be within the range of relevant acoustic impedances of tissue, such as between 1 megarayl (MRayl) and 6 MRayl, at frequencies generated by a corresponding ultrasound probe to which the gel standoff may be attached. Phase change gel pad materials (e.g., phase changing materials), methods of activation, and related benefits are also described herein. Accordingly, the gel standoffs may significantly improve image quality relative to fluid-filled caps, while providing the same or superior ultrasound therapy and imaging capabilities.

With the foregoing in mind, FIG. 1 is a schematic representation of a system 10 for neuromodulation. Such a neuromodulation system 10 may be used to achieve neurotransmitter release and/or activate components (e.g., the presynaptic cell, the postsynaptic cell) of a synapse in response to an application of ultrasound energy. The depicted system includes a pulse generator 14 coupled to an energy application device 12 (e.g., an ultrasound transducer). The energy application device 12 is configured to receive energy pulses, e.g., via leads or wireless connection, that in use are directed to a region of interest of an internal tissue or an organ of a subject, which in turn results in a change in a local and/or systemic change in concentration of a biologically active molecule, process, or function, such as changes to a concentration of a glucose transporter pathway molecule and/or an incretin pathway molecule in the context of a metabolic disorder treatment.

In certain embodiments, the energy application device 12 and/or the pulse generator 14 may communicate wirelessly, for example with a controller 16 that may in turn provide instructions to the pulse generator 14. In other embodiments, the pulse generator 14 may be an extracorporeal device, e.g., may operate to apply energy transdermally or in a noninvasive manner from a position outside of a subject's body, and may, in certain embodiments, be integrated within the controller 16. In embodiments in which the pulse generator 14 is extracorporeal, the energy application device 12 may be operated by a caregiver and positioned at a spot on or above a subject's skin such that the energy pulses are delivered transdermally to a desired internal tissue. Once positioned to apply energy pulses to the desired site, the system 10 may initiate neuromodulation of one or more target internal sites to achieve clinical effects such as treatment of a metabolic disorder.

In certain embodiments, the system 10 may include an assessment device 18 that is coupled to the controller 16 and assesses characteristics that are indicative of whether the changes in a patient characteristic of interest, such as changes in a glucose transporter pathway molecule and/or an incretin pathway molecule, as a result of the neuromodulation have been achieved. In one embodiment, the characteristics may be local. For example, the modulation may result in local tissue or function changes, such as tissue structure changes, local change of concentration of certain molecules, tissue displacement, increased fluid movement, etc.

The modulation may additionally or instead result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 18 may be configured to assess concentration changes of a molecule or molecules of interest in some embodiments. In some embodiments, the assessment device 18 may be an imaging device configured to assess changes in organ size and/or position. While the depicted elements of the system 10 are shown separately, it should be understood that some or all of the elements may be combined with one another. Further, some or all of the elements may communicate in a wired or wireless manner with one another.

Based on the assessment, the modulation parameters of the controller 16 may be altered. For example, if a desired modulation is associated with a change in concentration of a molecule of interest (circulating concentration or tissue concentration of one or more molecules) within a defined time window (e.g., 5 minutes, 30 minutes after a procedure of energy application starts) or relative to a baseline measurement at the start or before initiation of a procedure, a change of the modulation parameters such as pulse frequency or other parameters may be desired, which in turn may be provided to the controller 16, either by an operator or via an automatic feedback loop, for defining or adjusting the energy application parameters or modulation parameters of the pulse generator 14.

The system 10 as provided herein may provide energy pulses according to various modulation parameters. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. The treatment duration may last for various time periods, including, but not limited to, from a few minutes to several hours. In certain embodiments, treatment duration with a specified stimulation pattern may last for one hour, repeated at, e.g., 72-hour intervals. In certain embodiments, treatment may be delivered at a higher frequency, say every three hours, for shorter durations, for example, 30 minutes. The application of energy, in accordance with modulation parameters, such as the treatment duration and frequency, may be adjustably controlled to achieve a desired result.

Figure 2:
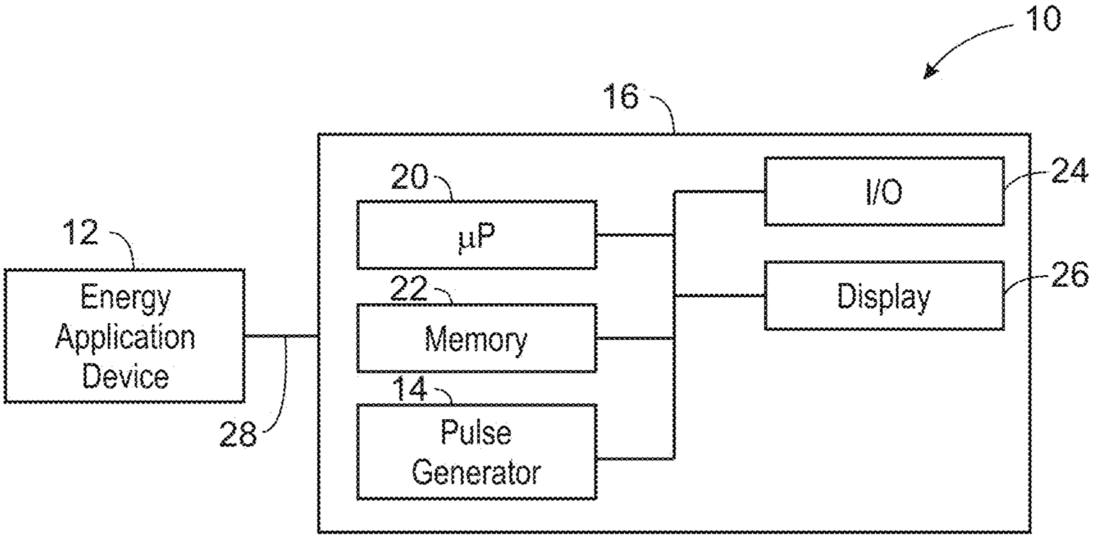
FIG. 2 is a block diagram of a neuromodulation system according to embodiments of the disclosure.

FIG. 2 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 20 for controlling the device. Software code or instructions are stored in memory 22 of the controller 16 for execution by the processor 20 to control the various components of the device. The controller 16 and/or the pulse generator 14 may be connected to the energy application device 12 via one or more leads 33 or wirelessly.

The controller 16 also includes a user interface with input/output (I/O) circuitry 24 and a display 26 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to the control signals from controller 16 to vary the stimulation characteristics of energy pulses transmitted through lead 28 to a subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 16 permits adjustably controlling the energy by changing the modulation parameters and/or initiating energy application at certain times or cancelling/suppressing energy application at certain times. In one embodiment, the adjustable control of the energy application device is based on information about a concentration of one or more molecules in the subject (e.g., a circulating molecule). If the information is from the assessment device 18, a feedback loop may drive the adjustable control. For example, if a circulating glucose concentration in blood or urine, as measured by the assessment device 18, is above a predetermined threshold or range, the controller 16 may initiate energy application to a region of interest (e.g., liver) and with modulation parameters that are associated with a reduction in circulating glucose. The initiation of energy application may be triggered by the glucose concentration drifting above a predetermined (e.g., desired) threshold or outside a predefined range. In another embodiment, the adjustable control may be in the form of altering modulation parameters when an initial application of energy does not result in an expected change in a targeted physiological outcome (e.g., concentration of a molecule of interest) within a predefined time frame (e.g., 1 hour, 2 hours, 4 hours, 1 day).

In one embodiment, the memory 22 stores different operating modes that are selectable by the operator. For example, the stored operating modes may include instructions for executing a set of modulation parameters associated with a particular treatment site, such as regions of interest in the liver, pancreas, gastrointestinal tract, spleen. Different sites may have different associated modulation parameters. Rather than having the operator manually input the modes, the controller 16 may be configured to execute the appropriate instruction based on the selection. In another embodiment, the memory 22 stores operating modes for different types of treatment. For example, activation may be associated with a different stimulating pressure or frequency range relative to those associated with depressing or blocking tissue function. In a specific example, when the energy application device is an ultrasound transducer, the time-averaged power (temporal average intensity) and peak positive pressure are in the range of 1 $mW/cm^2$-30,000 $mW/cm^2$ (temporal average intensity) and 0.1 MPa to 7 MPa (peak pressure). In one example, the temporal average intensity is less than 35 $W/cm^2$ in the region of interest to avoid levels associated with thermal damage & ablation/cavitation. The selected frequencies may depend on the mode of energy application.

In another embodiment, the memory 22 stores a calibration or setting mode that permits adjustment or modification of the modulation parameters to achieve a desired result. In one example, the stimulation starts at a lower energy parameter and increases incrementally, either automatically or upon receipt of an operator input. In this manner, the operator may achieve tuning of the induced effects as the modulation parameters are being changed.

The system may also include an imaging device that facilitates focusing the energy application device 12. In one embodiment, the imaging device may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 22 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 12 may be focused on the selected volume corresponding to the region of interest. For example, the energy application device 12 may be configured to first operate in the targeting mode to apply a targeting mode energy that is used to capture image data to be used for identifying the region of interest. The targeting mode energy is not at levels and/or applied with modulation parameters suitable for preferential activation at the region of interest. However, once the region of interest is identified and targeted, the controller 16 may then operate in a treatment mode according to the modulation parameters associated with preferential activation.

The controller 16 may also be configured to receive inputs related to the targeted physiological outcomes as an input to the selection of the modulation parameters. For example, when an imaging modality is used to assess a tissue characteristic, the controller 16 may be configured to receive a calculated index or parameter of the characteristic. Based on whether the index or parameter is above or below a predefined threshold, the modulation parameters may be modified. In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 (e.g., an ultrasound transducer) may operate under control of the controller 16 to: (a) acquire image data of a tissue that may be used to spatially select a region of interest within the target tissue, (b) apply the modulating energy to the region of interest, and (c) acquire an image to determine that the targeted physiological outcome associated with a change in a characteristic of interest has occurred (e.g., a change in a glucose transporter pathway molecule and/or an incretin pathway molecule has occurred (e.g., via displacement measurement)). In such an embodiment, the imaging device, the assessment device 18 and the energy application device 12 may be the same device.

In another implementation, a desired modulation parameter set may also be stored by the controller 16. In this manner, subject-specific parameters may be determined. Further, the effectiveness of such parameters may be assessed over time. If a particular set of parameters is less effective over time, the subject may be developing insensitivity to activated pathways. If the system 10 includes an assessment device 18, the assessment device 18 may provide feedback to the controller 16. In certain embodiments, the feedback may be received from a user or an assessment device 18 indicative of a characteristic of the target physiological outcome. The controller 16 may be configured to cause the energy application device to apply the energy according to modulation parameters and to dynamically adjust the modulation parameters based on the feedback. For example, based on the feedback, the processor 20 may automatically alter the modulation parameters (e.g., the frequency, amplitude, or pulse width of an ultrasound beam or mechanical vibration) in real time and responsive to feedback from the assessment device 18.

Figure 3:
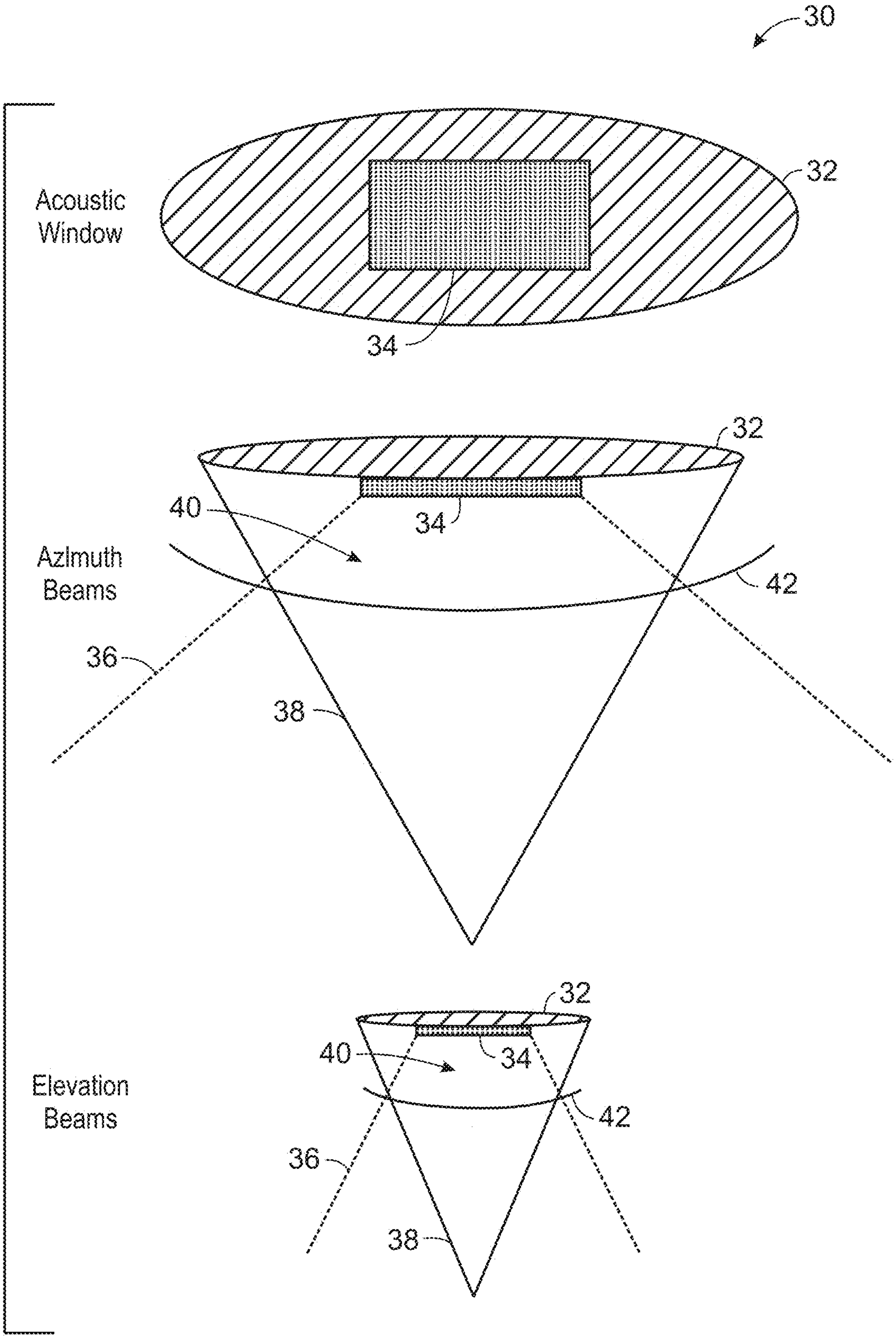
FIG. 3 is a schematic of a transducer arrangement with a gel standoff used in clear path determination, according to embodiments of the present disclosure.

With the foregoing in mind, FIG. 3 is a schematic 30 of a transducer arrangement with a standoff as discussed herein suitable for use in clear path determination in a therapeutic neuromodulation context and in accordance with embodiments of the present disclosure. It should be noted that the transducer arrangement is described by way of example only and some components may be omitted and/or additional components included. For example, an ultrasound probe in this context may include therapy transducers 32 and imaging transducers 34. In the depicted example a co-centric transducer configuration is illustrated in which the imaging transducer 34 array is centrally positioned, though a side-by-side configuration may also be suitable. In this way, the imaging beam 36 generated by the imaging transducers 34 encompasses substantially or entirely the full acoustic window of the therapy beam 38 generated by the therapy transducers 32. Accordingly, determining a clear path for an ultrasound beam may include that a determination that a target region in a patient for therapy is "visible" (i.e., resides within an imaging beam 36) and is accessible by a therapy beam 38.

In certain implementations, the therapy transducers 32 and imaging transducers 32 are separated from a patient by a gel standoff 40, as discussed herein. The disclosed gel standoff 40, as described herein, may be customized (e.g., sized or dimensioned) to ensure coverage of the therapy beam 38 path by the imaging beam 36 path at the patient interface onward in at least one dimension). Furthermore, unlike conventional standoffs that utilize a fluid-filled standoff with ultrasound coupling gel, the application surface 42 of the gel standoff 40 may be directly applied to the patient's skin. For example, use of coupling gel may involve multiple applications during a patient imaging/therapy session. Further, excess and dried coupling gel may need to be cleaned from the patient's skin after the session. In this way, the gel standoff 40 improves patient experience.

Figure 4A:
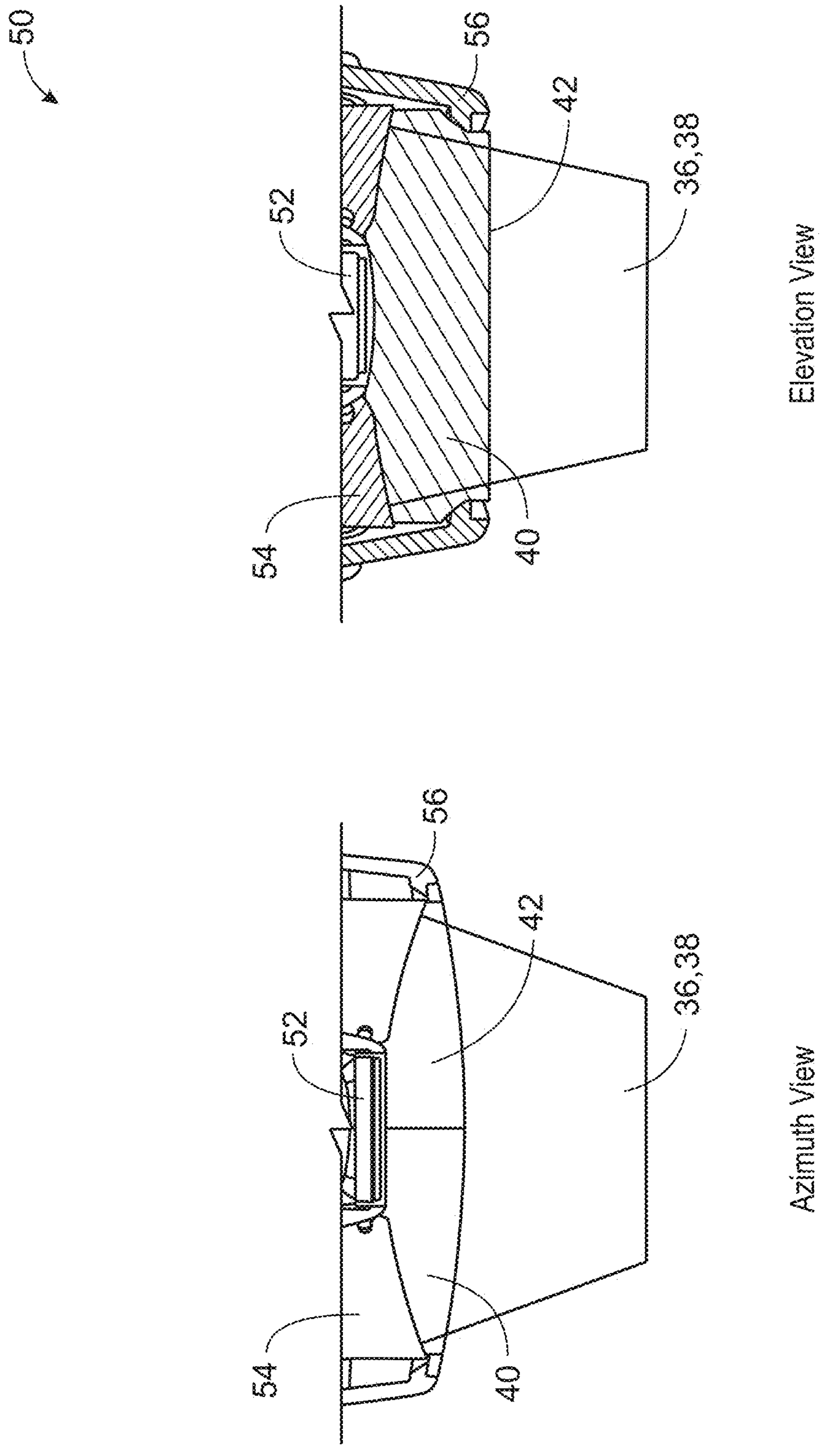
FIG. 4A is a schematic of a patient-facing portion of an ultrasound probe with the gel standoff, according to embodiments of the disclosure.

With respect to the implementation and use of the gel standoff 40, FIG. 4A is a schematic 50 of patient-facing portions of an ultrasound probe with the gel standoff 40. Two different views are presented that correspond to an azimuth view (leftmost figure) and an elevation view rotated 90° relative to the azimuth view (rightmost figure). The disclosed gel standoff 40 exhibits many advantages, such as providing desirable acoustic properties, good image quality, and little to no mess, thereby improving patient experience and clinical outcomes. In the depicted example of FIG. 4A, the probe includes imaging transducer 52 and therapy transducer 54. In some embodiments, the transducers may be co-centric or adjacently attached. The ultrasound probe may include one or more mating features 56, which enable the gel standoff 40 to snap into the cavity of the ultrasound probe and be held in place by the mating features 56. In this way, the gel standoff 40 separates the transducers from the application surface 42. The rightmost figure depicts an example of the one or more mating features 56, wherein a partial annular ridge may be used to enable a snap fit of the gel standoff 40 within the cavity. It should be noted that one or more mating features 56 may be utilized to create a fit alone or in combination with one another, including, but not limited to, a snap fit, mating ridges (e.g., interference snap fit), cantilever snap fit, annular snap fit, or a torsional fit (i.e., screw-in). The exemplary mating features 56 described herein would complement the material properties of the gel standoff 40 as they would leverage the flexibility (e.g., low modulus) of the gel standoff 40 such that the material can elastically deform during insertion and rebound to create an interference force, thereby allowing the ultrasound probe and gel standoff 40 to come into contact and be held together. As such, the mating features 56 enable a firm fit of the gel standoff 40 within the cavity of the probe and enable acoustic coupling at the transducer face for transmission and/or receipt of ultrasound energy of the imaging beam 36 and/or therapy beam 38 (e.g., beams 36, 38).

In general, the gel standoff 40 exhibits many advantages, such as replacing the need for an internal coupling oil/liquid, removing the need for ultrasound gel, and can be designed to accommodate multiple configurations of ultrasound probes to best fit different patients and/or target locations on a patient's body. Furthermore, the gel standoff 40 can be made to be a single-use/disposable. As such, the gel standoff 40 creates a more hygienic process. Importantly, the conformable (or otherwise not rigid) composition of the gel standoff 40 also enables a more accurate positioning (e.g., angle, X-Y position) of the ultrasound probe onto a patient's body, allowing the probe to conform to a target location. In this way, the gel standoff 40 provides various customization opportunities to enable good acoustic coupling.

Figure 4B:
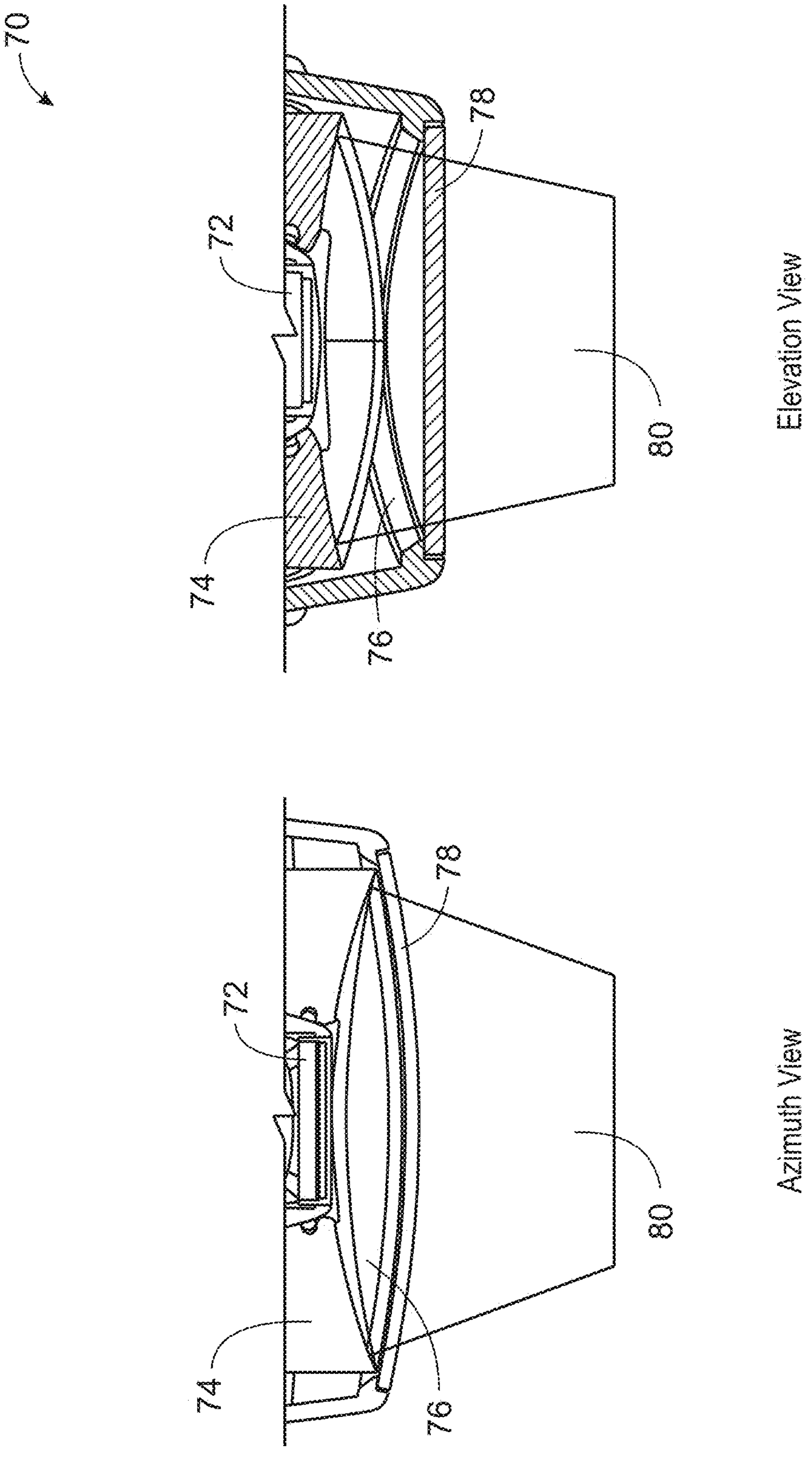
FIG. 4B is a schematic of a patient-facing portion of an ultrasound probe with a standard cap arrangement.

By way of comparison, FIG. 4B is a schematic 70 of patient-facing portions of an ultrasound probe with a standard cap arrangement. Two different views are presented that correspond to an azimuth view (leftmost figure) and an elevation view rotated 90° relative to the azimuth view (rightmost figure). The ultrasound probe is depicted having imaging transducers 72, therapy transducers 74, a standoff 76 (e.g., fluid-filled standoff as shown, or a solid standoff (not shown)), and a standard cap 78 (e.g., hard plastic). In general, the internal standoff 48 separates the transducers from the standard cap 78. In some embodiments, the transducers may be co-centric or otherwise adjacently attached with a co-molded lens or fluid filled cap over both transducers. Due to the design and type of standoff 76 (e.g., fluid-filled standoff), this implementation of a probe necessitates the use of ultrasound coupling gel. As such, the fluid-filled standoff exhibits many issues such as acoustic reverberations resulting in poor image quality relative to the gel standoff 40 as depicted in FIG. 4A.

Figure 5:
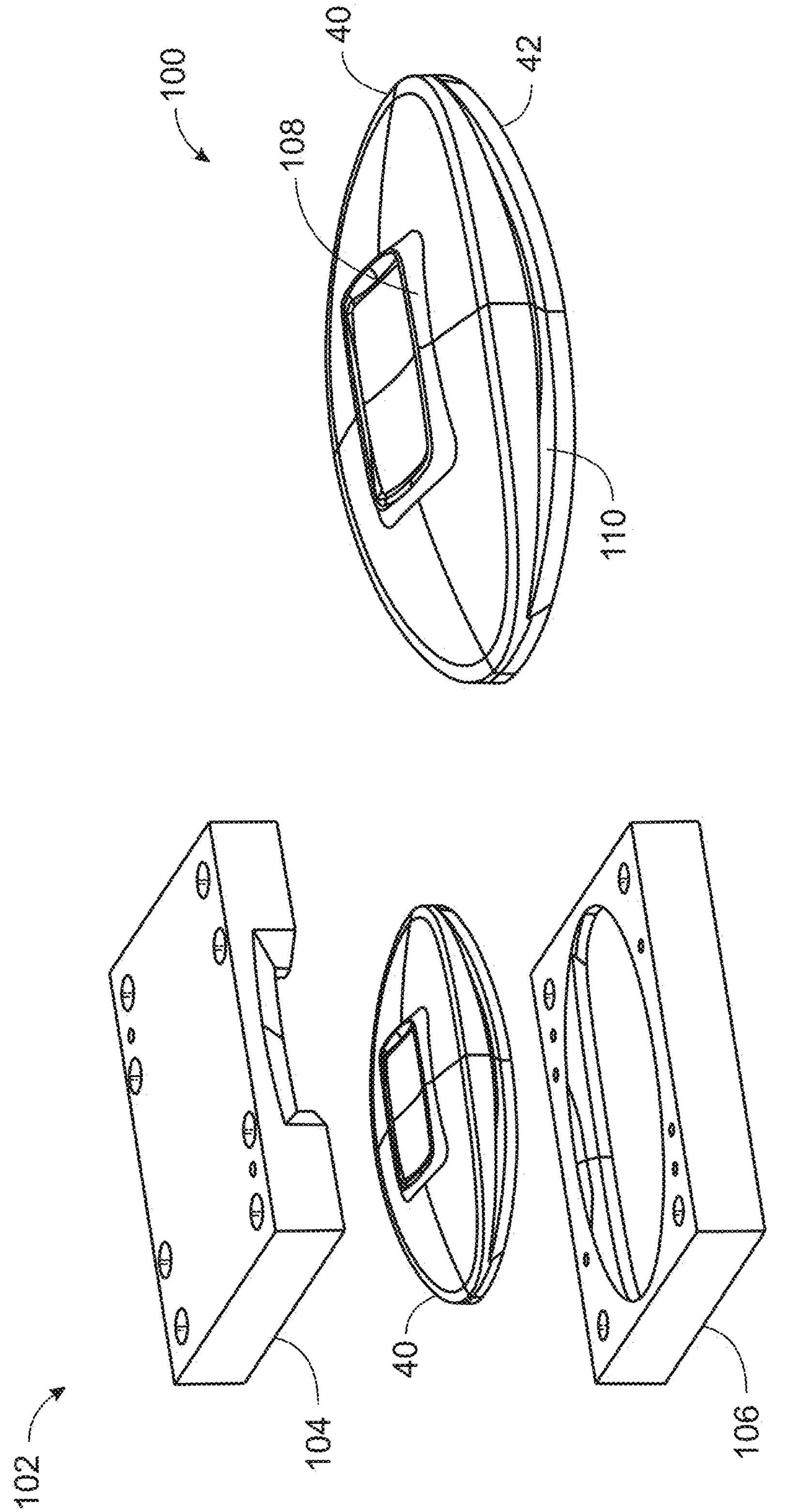
FIG. 5 is a schematic of a mold to produce the gel standoff, according to embodiments of the present disclosure.

With the preceding in mind, FIG. 5 is schematic 100 of a mold 102 that may be used to produce the gel standoff 40 according to embodiments of the present disclosure. The mold 102 may exhibit or otherwise include structural features (e.g., ridges, grooves, edges, X/Y/Z dimensionality) that enable the mold 102 to create and/or impart geometrical features upon the gel standoff 40 during the molding process. In certain implementations, one or more such features may facilitate the engagement of the gel standoff 40 with an ultrasound probe. Accordingly, the gel standoff 40 may be produced by providing one or more materials (e.g., hydrogel, solid oil) into the mold 102, such as in a first flowable or malleable state and allowing the material to set or otherwise rigidify to a second state within the mold which is no longer flowable. In practice the mold 102 may include an upper template 104 and a lower template 106 that individually and/or together create one or more geometrical features upon the molded gel standoff 40. By way of example, in one embodiment the upper template 104 may include features (e.g., ridges, edges, or grooves) that create a transducer mating profile 108 during the molding process. The transducer mating profile 108 allows one or more transducers of an ultrasound probe to reversibly mate or couple to the gel standoff 40. Accordingly, the transducer mating profile 108 allows for intimate contact between the transducer-side surface of the gel standoff 40 and the transducers and enables good acoustic coupling when mounted to a probe due to its ability to minimize air pockets between the gel standoff 40 and the transducers.

Similarly, in certain embodiments the lower template 106 may be utilized during the molding process to generate an application or patient facing surface (e.g., bottom of the gel standoff 40). In such an embodiment the lower template 106 may also include features (e.g., ridges, edges, or grooves) similar to the upper template 104 to create a retaining groove 110 (or other snap and interference fit structural feature(s)) that may couple with one or more mating features 56 of an ultrasound probe. The retaining groove 110 allows the gel standoff 40 to lock and or couple with a complementary one or more mating features 56 (e.g., one or more mating features 56 of probe acts as a male alignment feature, retaining groove 110 acts as a female alignment feature) of the ultrasound probe so as to hold the molded gel standoff 40 in place. With this geometrical feature, the gel standoff 40 may push and/or snap on and stay locked in place for the duration of a treatment session. As such, the retaining groove 110 allows the gel standoff 40 to reversibly mate or couple with the one or more mating features 56 of the ultrasound probe. The lower template 106 may also generate an application surface 42 (e.g., patient-facing surface). The application surface 42 of the gel standoff 40 allows for the standoff to be directly applied to a patient's body and/or skin without the need for ultrasound coupling gel. In some embodiments, the upper template 104 may include features to generate the retaining groove 110. Accordingly, it should be noted that the mold 102 (e.g., upper template 104 and lower template 106) may be configured or customized to include additional features to create gel standoffs 40 to accommodate alternative ultrasound probe configurations and/or transducer configurations.

In general, the embodiments described herein allow for gel standoffs 40 to be customized to accommodate a variety of patient body type as well as various neuromodulation applications or needs. For example, in certain embodiments, gel standoffs 40 may be molded out of a single material or composition, such as a hydrogel or a phase change material (e.g., a solid oil, a phase changing material). In some embodiments, the gel standoff 40 may be molded from multiple materials or compositions, such as to create a multi-layered construct or, more generally, a gel standoff 40 having discernible structure or features (i.e., non-uniform) formed within, such as by using different compositions for the different internal features. In other embodiments, the gel standoff 40 may be molded of a combination of multiple materials, which may improve acoustic performance by removing or reducing (e.g., by forming a gradient or transition (i.e., a gradient-based material)) abrupt transitions or boundaries attributable to a multi-layered construction and thereby reduce or eliminate reflections attributable to such boundaries. As such, the material and/or structural properties of the gel standoff 40 may be chosen to spatially configure certain desired acoustic properties, such as attenuation and impedance.

Compositions of the gel standoff 40 may include, but are not limited to, biocompatible, cross-linked hydrogels such as polyacrylamide, acrylate-siloxane, alkoxysilane, hyaluronic acid and derivatives, and co-polymers and derivatives thereof. Additionally, hydrogels may be loaded with or otherwise include additives other than water, which can aid in maintenance of lubricity on skin while maintaining intimate coupling (e.g., water soluble additives-glycerin, polyethylene glycol or hydrophobic additives). Alternatively, synthetic, non-hydrogel elastomeric materials may be utilized, including, but not limited to, highly plasticized polyurethanes (e.g., plasticized elastomeric polymer), and divinyl olefin polymers. Additives may be formulated into any of these materials to increase lubricity, prevent drying and prevent skin irritation. Exemplary materials include silicones (dimethicone, cyclomethicones (e.g., cyclopentasiloxane)), fatty acid esters (e.g., palmitates) and other moisturizing ingredients commonly used in skincare.

Furthermore, the gel standoff 40 may be customized to exhibit a thickness (e.g., in the Z-direction) ranging from about 0.5 to about 6 centimeters (cm), such as about 0.5 to about 5 cm, about 0.5 to about 4 cm, about 0.5 to about 3 cm, about 0.5 to about 2 cm, or about 1 to 2 cm. The gel standoff may exhibit an area in the X-Y dimension no greater than about 200 $cm^2$. For example, for a concentric transducer arrangement with an outer circular therapy transducer having a 6 cm diameter, the gel standoff may be about 6 cm in diameter in the X-Y direction (area of approximately 28.3 $cm^2$) to enable good acoustic coupling across the entire surface of the transducers and sufficient contact with a patient's skin. In general, the dimensions of the gel standoff 40 and/or the geometry of the gel standoff 40 may be customized based on the transducer geometries, patient's body type and/or targeted location. For example, a gel standoff 40 may be customized to be thinner overall or thinner in certain regions such that it may conform properly to patients with high body mass index (BMI) (e.g., obese patients) and deliver ultrasound energy accordingly. Alternatively, a patient with a low BMI may need a gel standoff 40 that is thicker overall or in certain regions to better direct the ultrasound energy to a region of interest. In this way, the gel standoff 40 presents various advantages to accommodate a variety of neuromodulation applications to treat various clinical conditions.

Figure 6:
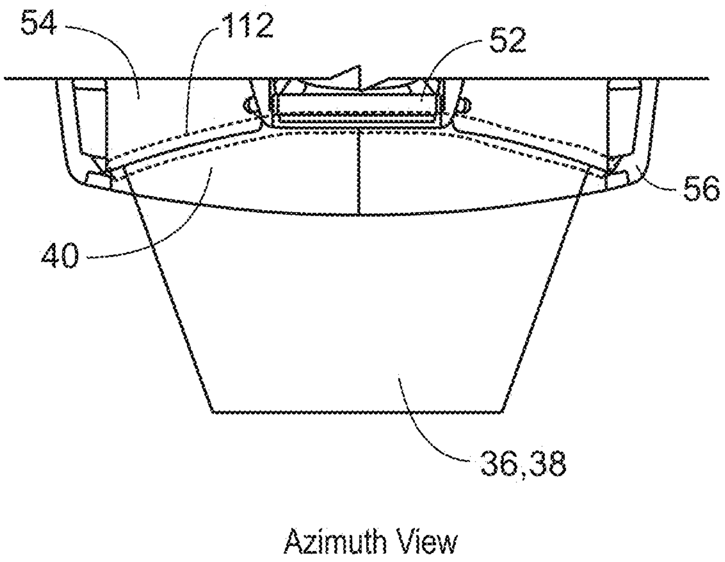
FIG. 6 depicts a schematic view of a patient-facing portion of an ultrasound probe with a gel standoff arrangement in use with an example of the gel standoff, according to embodiments of the present disclosure.

By way of example, FIG. 6 depicts a schematic view of a patient-facing portion of an ultrasound probe with the gel standoff 40 of FIG. 4A according to embodiments of the present disclosure. As discussed with respect to FIG. 4A, the gel standoff 40 may be custom molded to fit the transducer geometry such that after insertion, there is good coupling of acoustic energy from the transducer into the gel standoff 40. As such, and as shown in the present examples, there are no air gaps between the transducers and the transducer-side of the gel standoff 40, represented by line 112. Based on the composition of the gel standoff 40, the gel standoff 40 may be pre-wetted to ensure good coupling. For example, the gel standoff 40 may be dipped or sprayed with water on the transducer-side prior to insertion into an ultrasound probe. In some embodiments, the gel standoff 40 may be "wet" packaged such that it is ready for insertion out of the package. In other embodiments, the material composition of the gel standoff 40 may be naturally "wet" (e.g., self-wetting material) or change phase to become "wet" during use. In this way, the gel standoff 40 may enable good coupling of acoustic energy from the transducers. In some embodiments, the gel standoff 40 may consist of a uniformly or evenly distributed material (e.g., a single material composition, such as where the gel standoff consists solely of a hydrogel or a solid oil).

Figure 7:
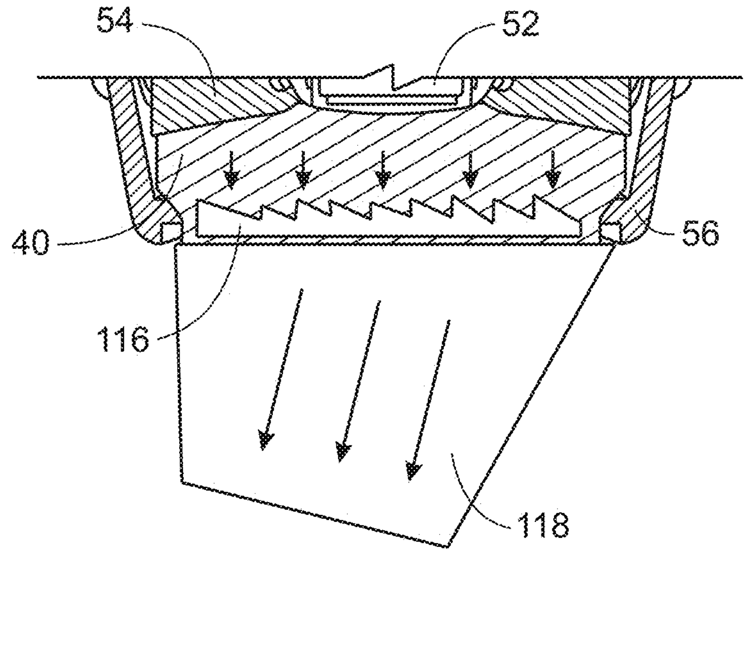
FIG. 7 depicts a schematic view of a patient-facing portion of an ultrasound probe with the gel standoff arrangement in use with an example of the gel standoff with a complex construction, according to embodiments of the present disclosure.

With the foregoing in mind, FIG. 7 depicts a schematic view of a patient-facing portion of an ultrasound probe with the gel standoff 40 of FIG. 4A with a complex construction. The gel standoff 40 may have a more complex construction, such as being customized and/or being fabricated using multiple materials to create a multi-layered standoff or a multiple-material standoff to provide desirable acoustic properties based on the properties of the standoff. For example, an ultrasound probe with a gel standoff 40 having internal structure or features and/or multiple layers (FIG. 7) may be used, wherein the gel standoff 40 may be configured so as to include a lens 116. The lens 116 may be incorporated into the gel standoff 40 to provided desired focusing in azimuth, elevation, and/or depth, as demonstrated by the angled beam path 118 and may be made from a rigid or non-rigid material. Accordingly, the lens 116 (e.g., lens material) could be designed to exhibit various shapes to accommodate different patients' body geometries, target anatomical regions at various depths, and/or to help angulate the beam (e.g., imaging beam, therapy beam) toward a target or region of interest. Thus, the gel standoff 40 provides customizable focusing for neuromodulation applications.

Figure 8:
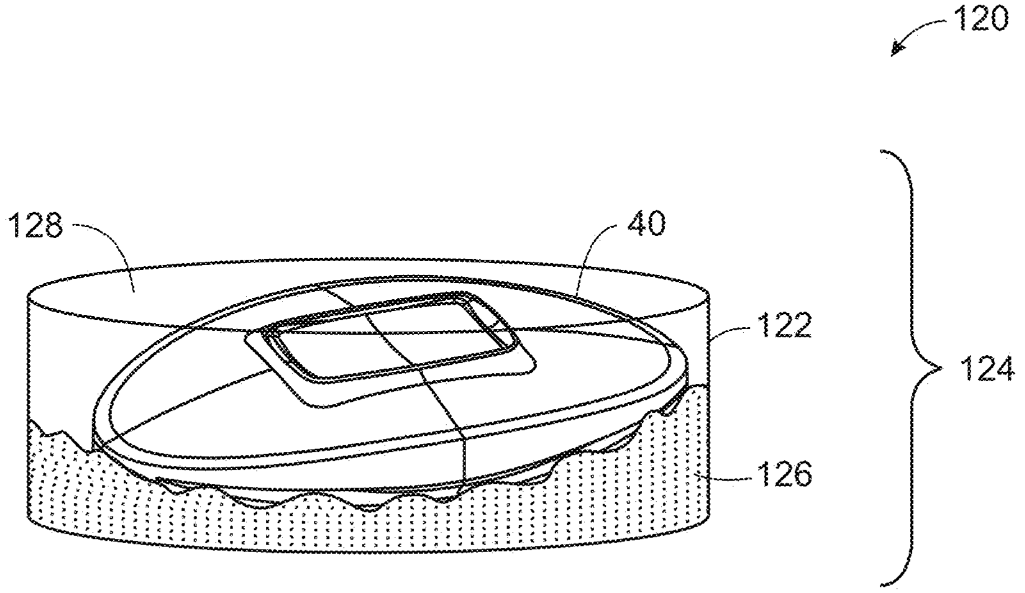
FIG. 8 is a schematic of a gel standoff stored in a container, according to embodiments of the present disclosure.

With the preceding in mind, FIG. 8 is a schematic view 120 of the gel standoff 40 stored in a container 122 provided as part of a disposable gel pad pack 124 according to embodiments of the present disclosure. The gel standoff 40 may be packaged in the container 122 with fluid as part of the gel pad pack 124, thereby allowing the gel standoff 40 to be provided to a user as a disposable, single-use product. The container 122 may also contain a lid 128 (e.g., a plastic cover) to suitably contain the gel standoff 40 and fluid solution or water bath 126 (e.g., packing or wetting fluid) during shipping and storage. For example, the container 122 may include the gel standoff 40 stored in a fluid solution or water bath 126. In particular, gel standoffs 40 made of hydrogel may be stored in a fluid solution or water bath 126. In some embodiments, a fluid solution or water bath 126 may not be present for gel standoffs 40 made of solid oil. As such, the container 122 may be designed to facilitate or otherwise accommodate good acoustic coupling between transducers of an ultrasound probe and the gel standoff 40. For example, the container 122 may be large enough such that a user may bring the container 122 towards the transducers (e.g., probe head) of the ultrasound probe to insert/lock the gel standoff 40 into place. Accordingly, the gel standoff 40 may be packaged into a kit and utilized on an individual patient basis.

Figure 9:
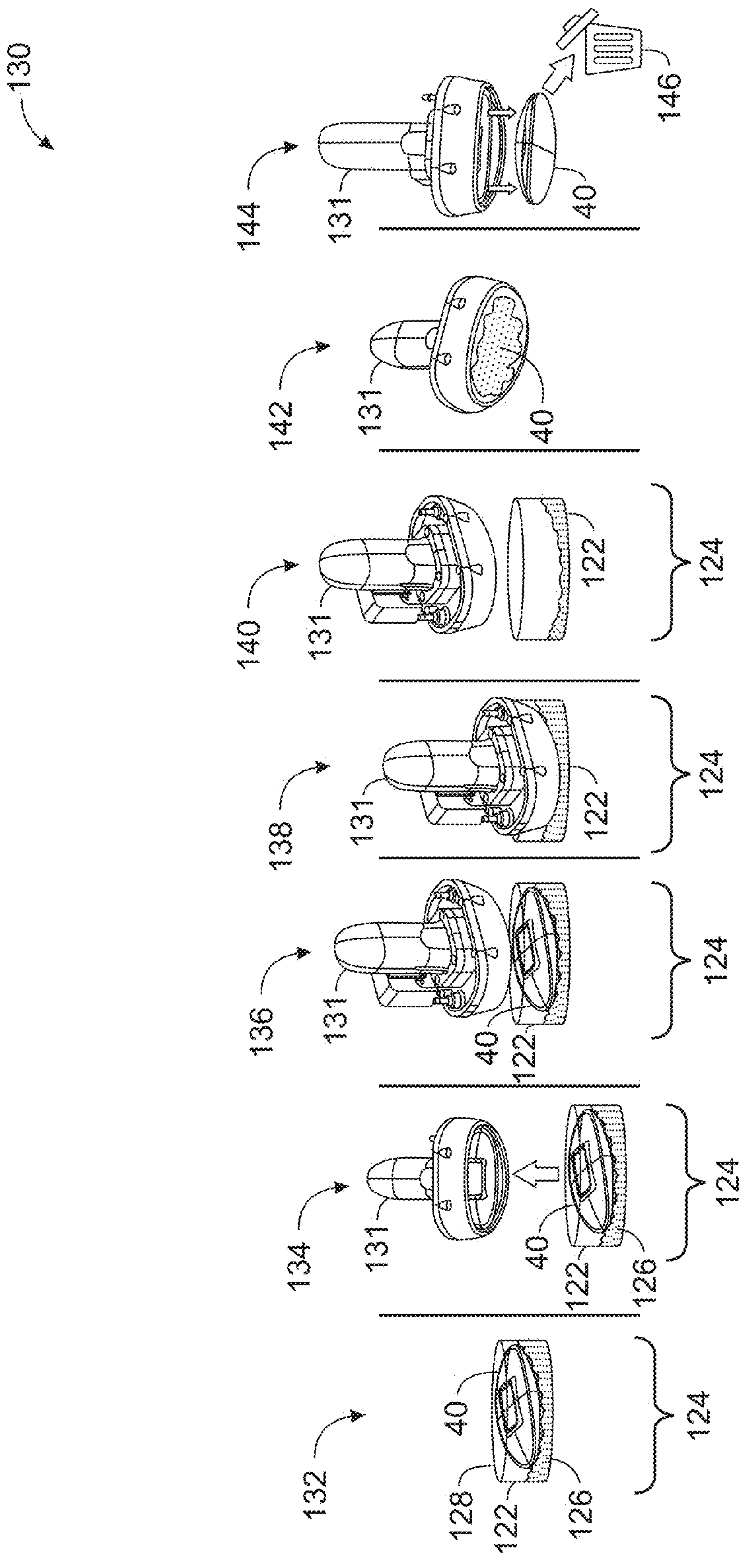
FIG. 9 is an example workflow of one method for mounting a gel standoff onto an ultrasound probe, according to embodiments of the present disclosure.

Turning to FIG. 9, an example workflow is provided of a method 130 of mounting the gel standoff 40 onto an ultrasound probe according to embodiments of the present disclosure. The method 130 includes various steps represented by images. Although the example workflow illustrates the steps in a certain sequence, it should be understood that the steps may be performed in any suitable order and certain steps may be carried out simultaneously, where appropriate. Additionally, steps may be added to or omitted from the method 130.

The method 130 may begin at step 132, wherein a user may obtain a disposable gel pad pack 124 (e.g., gel standoff 40 in container 122) in preparation for application of ultrasound energy to cause neuromodulation in a patient. As previously described in FIG. 7, the gel pad pack 124 may include the gel standoff 40 in a container 122, and the gel standoff 40 may be stored in a fluid solution or water bath 126 and be secured in the container 122 by the lid 128. As such, the user may begin by first removing the lid 128 (or peeling off a thin plastic cover) from the container 122. The user may, in some embodiments, briefly rinse the gel standoff 40 within the container 122 with water or other suitable fluid to wet the gel standoff 40.

At step 134, the user may prepare for insertion of the gel standoff into a complementary volume formed as part of an ultrasound probe 131, such as formed in part of a probe head of the ultrasound probe. This may be accomplished by bringing the pad pack 124 towards the ultrasound probe 131. Subsequently, at step 136, the user may align the central axis of the ultrasound probe 131 down onto the gel pad pack 124 that contains the gel standoff 40. As described in FIG. 5, the gel standoff 40 and ultrasound probe may include complementary features (e.g., male/female or slot and groove alignment features) to allow the gel standoff 40 to securely engage with the ultrasound probe 131. For example, the gel standoff 40 and ultrasound probe 131 may include geometric features such as grooves and ridges (e.g., transducer mating profile 108 and retaining groove 110) to enable the gel standoff 40 to securely engage with the cavity of the ultrasound probe 131. Similarly, the ultrasound probe 131 may include grooves and ridges to enable proper fitting of the gel standoff 40 within the cavity of the probe. Furthermore, the inner wall of the pad pack 124 may be dimensioned to match the outer dimensions of the ultrasound probe 131 to be inserted such that alignment of the ultrasound probe 131 to the pad pack 124 and/or gel standoff 40 may be easily achieved.

At step 138, the user may apply a pressing force onto the gel pad pack 124 so as to press the gel standoff 40 into engagement with the ultrasound probe 131 by pressing the gel standoff 40 in the gel pad pack 124 towards the ultrasound probe 131. This motion allows the gel standoff 40 to release contact from the gel pad pack 124 and "snap" or "suction" into place. In some embodiments, the ultrasound probe 131 may be pressed towards the gel pad pack 124. For example, the gel pad pack 124 may be placed onto a surface, upon which the ultrasound probe 131 may be pressed into the pad pack 124. Afterwards, at step 140, the user may lift the ultrasound probe 131 including the gel standoff 40 to release contact and separate away from the container 122. The user may throw away the remaining packaging of the gel pad pack 124.

At step 142, the user may apply or engage the ultrasound probe 131 (and the attached gel standoff 40) to the patient and subsequently perform ultrasound dosing to induce neuromodulation in a patient until completion of the neuromodulation protocol. Afterwards, at step 144, ultrasound probe 131 may be moved away from the patient and the gel standoff 40 may be removed from the ultrasound probe 131. For example, the ultrasound probe 131 may include an eject button to allow the gel standoff 40 to be released from the ultrasound probe 131. In this way, the gel standoff 40 may be disposed into the trash 146 accordingly. It should be noted that the ultrasound probe 131 may trap residue from the gel standoff 40. As such, the user may rinse the ultrasound probe 131 under water as needed (or otherwise perform a sanitizing procedure) until the remaining gel residue is removed. Accordingly, the gel pad pack 124 as described herein utilizes a water-based procedure that enables a no-touch workflow, thereby providing an overall positive user experience.

Figures 10A, 10B, 10C:
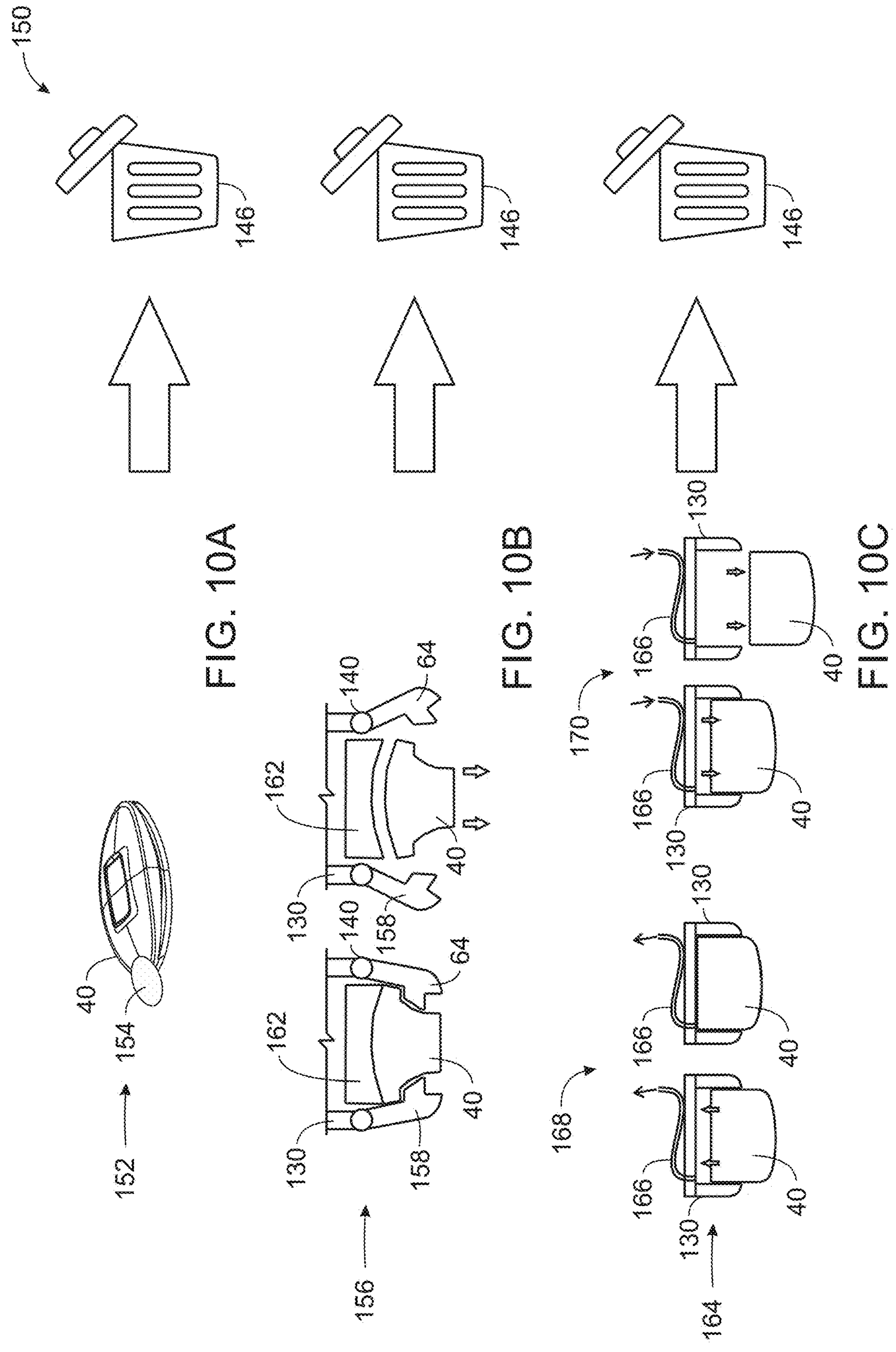
FIGS. 10A, 10B, and 10C schematically depict three example methods for removing a gel standoff from an ultrasound probe, according to embodiments of the present disclosure.

By way of example, FIGS. 10A, 10B, and 10C are schematic views 150 corresponding to different procedures for removing the gel standoff 40 from the ultrasound probe 131 according to different embodiments of the present disclosure. In certain implementations the gel standoff 40 is a disposable, single-use product. Accordingly, the gel standoff 40 may be removed after application of energy to a patient as part of a neuromodulation protocol. In one embodiment, the geometry of the gel standoff 40 may be designed to protrude sufficiently away from an outer lip of an ultrasound probe 131 such that the gel standoff 40 may be grasped and peeled out. In another embodiment, shown in FIG. 10A, a pull-tab method 152 may be utilized to remove the gel standoff 40. The gel standoff 40 may be designed with a pull-tab 154 structure that is attached to or integrally formed with the gel standoff 40 and may protrude from the side of an ultrasound probe 131 while the gel standoff 40 is secured. A user may remove the gel standoff 40 from the ultrasound probe 131 by holding the pull-tab 154 and peeling it out of the ultrasound probe 131 and disposing of it into the trash 146. The retaining groove 110 around the perimeter of the gel standoff 40 may be physically disengaged (e.g., uncoupled) in this manner from the complementary mating ridge 64 of the ultrasound probe, and the transducer mating profile 108 may disengage from the one or more transducers to release the gel standoff 40. The pull-tab 154 may be integrated into the gel standoff 40 during its molding process and thereby exhibit similar chemical compositions to the gel standoff (e.g., hydrogel or solid oil). Alternatively, in some embodiments, the pull-tab 154 may be designed with a different material that exhibits strong mechanical properties to withstand the pulling force. Accordingly, the insertion and removal of the gel standoff 40 is a reversible mating process through the presence of such geometrical features.

In another embodiment, shown in FIG. 10B, an edge-hinge method 156 may be used to remove the gel standoff 40 that is in contact with one or more transducers 162 within the ultrasound probe 131. For example, the ultrasound probe 131 may include a button or other mechanical actuation mechanism that controls the movement of one or more edges 158 of the ultrasound probe 131 via a hinge 160. For example, the hinge 160 may be a hinge with two discrete parts that rotate relative to one another. In some embodiments, the hinge 160 may be a flexural hinge configured to the cap of the ultrasound probe 131. Accordingly, the ultrasound transducer probe 131 with the flexural hinge may provide the necessary engagement of the lip-and-groove or other movable snap fit features. The edge 158 of the ultrasound probe 131 may be designed to include a mating ridge 64 that engages with the retaining groove of the gel standoff 40 to secure the gel standoff into the ultrasound probe 131 when the edge 158 is in an engaged configuration (FIG. 10B, left). In order to remove the gel standoff 40 from the ultrasound probe 131, a user may push the button (or other mechanical actuation mechanism) on the ultrasound probe 131 to release the edge 158 at the hinge 160 (placing the engagement mechanism in a dis-engaged configuration) and disengage the mating ridge 64 from the gel standoff 40 (FIG. 10B, right). In this way, the gel standoff 40 may be released and drop, after which a user may discard the standoff into the trash 146.

In some embodiments, shown in FIG. 10C, an air pump method 164 may be used to secure and remove the gel standoff 40 from the ultrasound probe 131. For example, the ultrasound probe 131 may be designed to include a valve 166 that controls the direction of airflow within a tube and engagement volume of the ultrasound probe 131. For example, the insertion step 168 (FIG. 10C, left) may include air being directed outward to create a partial vacuum in a cavity between the probe interior surface and the gel standoff 40. In response to the partial vacuum, the gel standoff 40 may be held securely within the cavity and residual air may be thereby removed, thereby improving the coupling between the transducer faces and the gel standoff 40. To remove the gel standoff 40, the removal step 170 (FIG. 10C, right) may include flowing air against the gel standoff 40 and into the cavity so as to create a relative overpressure within the cavity. The relative overpressure within the cavity effectively pushed the gel standoff 40 out from the cavity of the ultrasound probe 131, thereby allowing a user to discard the gel standoff 40 into the trash 146. It should be noted that additional components may be integrated as part of the air pump method to control the air pressure and/or direction of air flow to insert and remove the gel standoff 40 from the ultrasound probe 131. Furthermore, the gel standoff 40 may exhibit a different geometry such that it may be compatible with the air pump method. For example, the gel standoff 40 may not include some of the geometric features (e.g., transducer mating profile 108 and retaining groove 110).

Figure 11:
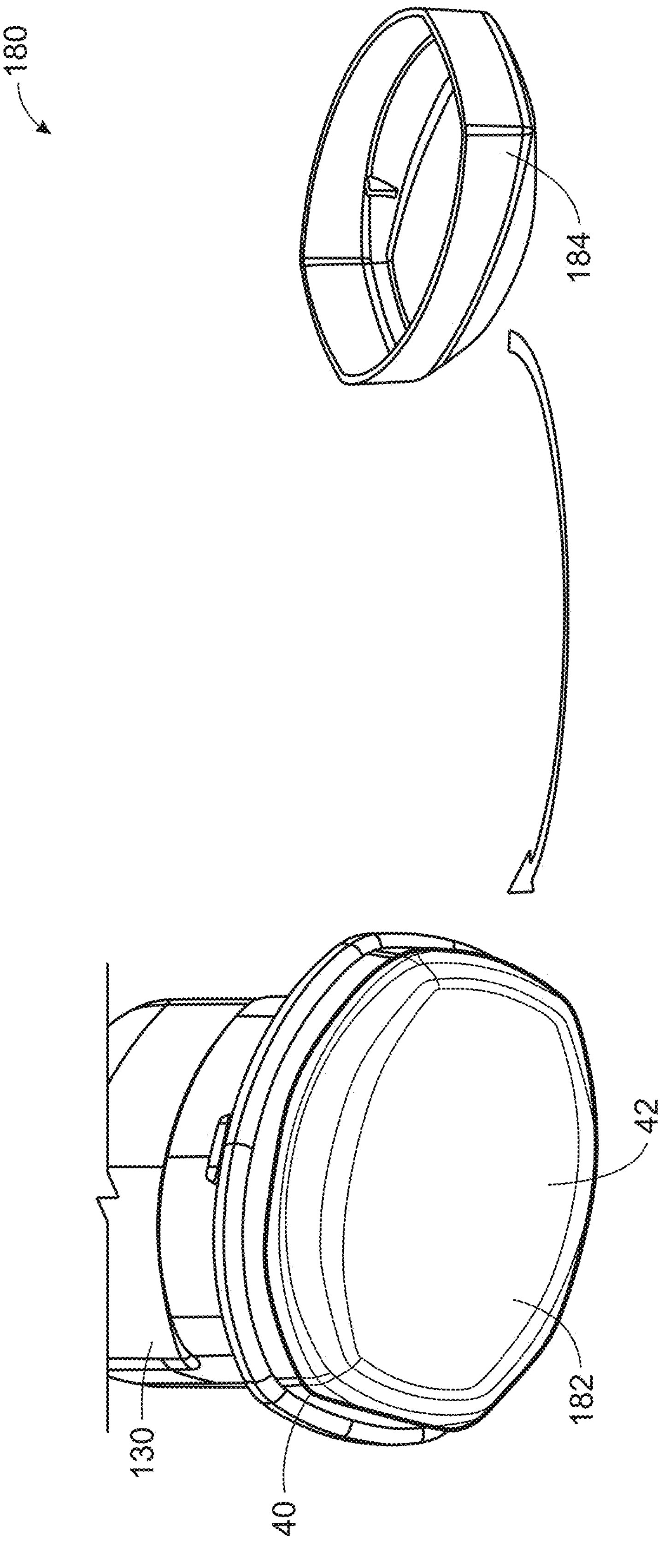
FIG. 11 is a schematic of alternative compositions of the gel standoff, according to embodiments of the present disclosure.

With the foregoing in mind, FIG. 11 is a schematic view 180 of the use of alternative compositions of the gel standoff 40 according to embodiments of the present disclosure. As described in FIG. 5, the composition of the gel standoff 40 may be designed in certain embodiments to include a single material, wherein the entirety of the gel standoff 40 is made of a hydrogel or a phase change material. In other embodiments, the gel standoff 40 may be designed as a multi-layered material. Accordingly, FIG. 11 illustrates how the gel standoff 40 may be designed as a multi-layered material. For example, the gel standoff 40 may be designed such that the application surface 42 (i.e., a surface or patient-facing layer) consists of a different material, wherein the transducer-side surface of the gel standoff 40 may be a hydrogel, and the patient side (i.e., application surface 42) of the gel standoff may be a phase change material 182 (e.g., solid oil, wax). The phase change material 182 in this context is a material that begins to undergo a phase change from a solid to a liquid due to its melting temperature coinciding generally with the temperature of the material with which it is in contact. Accordingly, a material may be selected that changes its phase to be "wet" upon contact at a patient's skin, which is presumably at a higher temperature point than ambient room temperature. For example, the phase change material may be a solid oil that is a solid at room temperature (e.g., about 25° C.) and that exhibits a melting temperature (i.e., begins to melt) ranging from about 30° C. to about 40° C. (e.g., average human temperature). For example, the phase change material may melt at temperatures ranging from about 33° C. to about 37° C. In this way, the phase change material 182 is self-wetting or may be naturally wet and may lubricate itself during the energy application process.

Furthermore, in other embodiments, a gel standoff 40 comprising a multi-layered material or a gradient-based material may be designed to exhibit properties such as elastic modulus, lubricity, and varying acoustic modulus. For example, the elastic modulus of the gel standoff 40 may be varied as a multi-layered material such that the application side exhibits a softer elastic modulus (e.g., soft material) for skin contact while the ultrasound probe side may exhibit a harder elastic modulus (e.g., hard material). The lubricity of the gel standoff 40 may be customized such that the application side exhibits a slippery surface for skin contrast. In contrast, the probe side of the gel standoff 40 may exhibit a stickier surface to enable good contact and fit of the gel standoff 40 into the cavity of an ultrasound probe. Furthermore, the gel standoff 40 may be customized with varying acoustic modulus to avoid reflections. For example, the gel standoff 40 may be molded of a combination of multiple materials to form a gradient-based material, which may improve acoustic performance by removing or reducing abrupt transitions or boundaries which may be associated with a gel standoff 40 of a multi-layered construction, thereby reducing or eliminating reflections attributable to such boundaries.

In another embodiment, the phase change material 182 may change phase not based on a change in temperature, but in response to the ultrasonic energy passing through as part of a therapy procedure. In other embodiments, the gel standoff 40 may be designed entirely of a single material (e.g., a hydrogel or solid oil) that begins to undergo a phase change at a patient contacting surface upon contact with a patient's skin. As such, the phase change material 182 may exhibit a gradient response with respect to temperature. For example, the phase change material 182 may exhibit higher melting temperatures near the transducers (e.g., near transducer side) and lower melting temperatures near the patient contact side (e.g., application surface 42). In some embodiments, a cap 184 may be designed whose composition consists of the phase change material 182. Accordingly, a user may secure or attach the cap 184 onto the gel standoff 40 prior to application of ultrasound energy to a patient's skin. It should be noted that the composition of the gel standoff may be selected such that it does not fully undergo a phase change during the energy application process. Furthermore, it should be noted that use of the phase change material 182 does not require any ultrasound gel to be utilized during energy application process. As such, ultrasound energy application (e.g., as part of a neuromodulation protocol) may be performed in the absence of the conventional ultrasound gel. In this way, the gel standoff 40 may be customized to provide good acoustic coupling and energy application to a patient.

Figure 12:
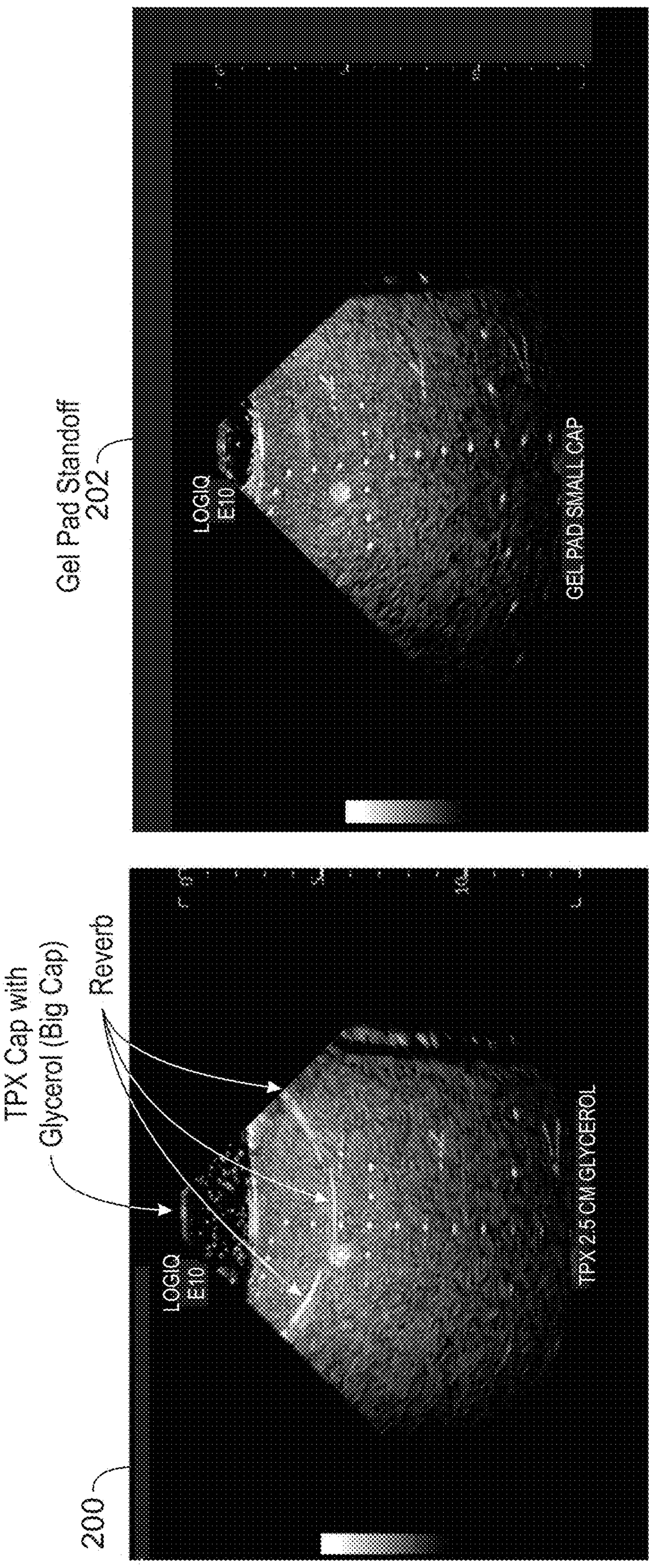
FIG. 12 is a comparison of ultrasound image quality acquired with a standard cap arrangement relative to the gel standoff, according to embodiments of the present disclosure.

FIG. 12 is a comparison of ultrasound image quality acquired with a standard cap arrangement 42 (e.g., fluid-filled cap) relative to the gel standoff. In general, ultrasound images 200 and 202 are images of wire targets in an ultrasound phantom. Ultrasound image 200 was acquired with the fluid-filled cap arrangement, wherein a polymethylpentene cap with glycerol was utilized, while ultrasound image 202 was acquired with the gel standoff 40. Accordingly, the gel standoff 40 enables high quality imaging with clear resolution of the wire targets, as demonstrated in ultrasound image 202. In contrast, the ultrasound image 200 acquired with the fluid-filled cap has a much higher reverb content and exhibits loss of image contrast and resolution. As such, the gel standoff 40 reduces reverberations and enables a significant improvement in image quality relative to fluid-filled caps.

Figure 13:
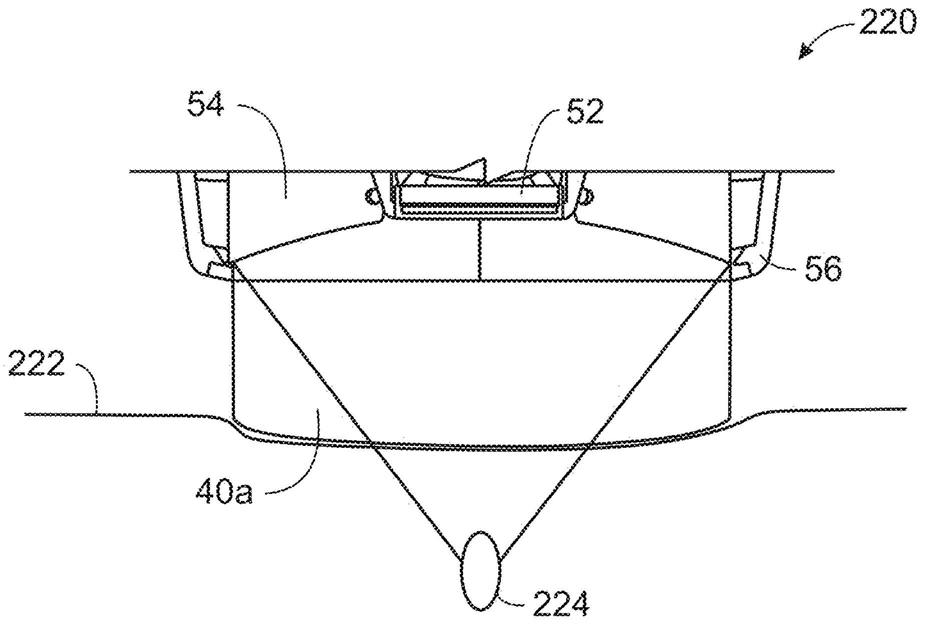
FIG. 13 is a schematic of a gel standoff with increased thickness, according to embodiments of the present disclosure.

By way of further example, FIG. 13 is a schematic 220 of a gel standoff 40*a* with increased thickness. In general, the schematic 220 includes the gel standoff 40*a*, wherein the gel standoff 40*a* is molded to exhibit an increased thickness relative to other examples described herein. Accordingly, when the gel standoff 40*a* is applied to a patient's surface 222, the increased thickness enables delivery of ultrasound energy (e.g., therapy beam and/or imaging beam) to target shallow anatomical features 222.

Figure 14:
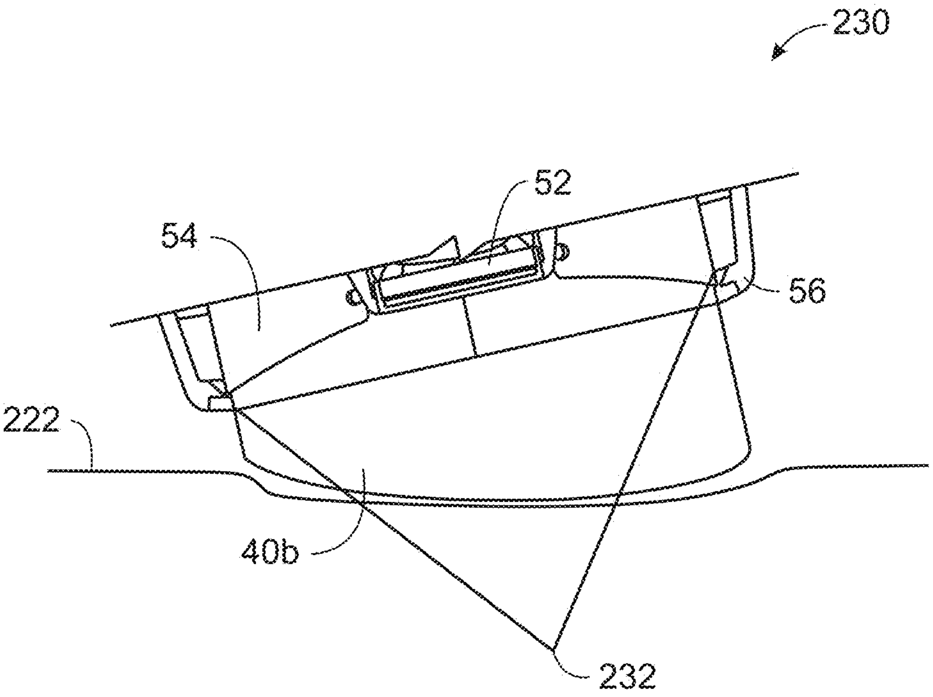
FIG. 14 is a schematic of an angulated gel standoff, according to embodiments of the present disclosure.

With the foregoing in mind, FIG. 14 is a schematic 230 of an angulated (e.g., pre-angulated) gel standoff 40*b*. In general, the schematic 230 includes the gel standoff 40*b*, wherein the angulated gel standoff 40*b* was molded to exhibit angle-like features. In this way, the angulated gel standoff 40*b* is applied to a patient's skin 222 and enables directing the therapy beam towards a target anatomy 232 for a particular ultrasound therapy application. The angulation could be in one or more degrees of freedom (DOF) to help pre-orient the ultrasound probe. Furthermore, if the ultrasound probe needs to be angled substantially relative to the patient skin 222, one side of the probe will naturally want to lift off. In this way, customizing the gel standoff 40*b* to be thicker on one side relative to the other may help to preserve the coupling of the gel standoff 40*b*.

Figure 15:
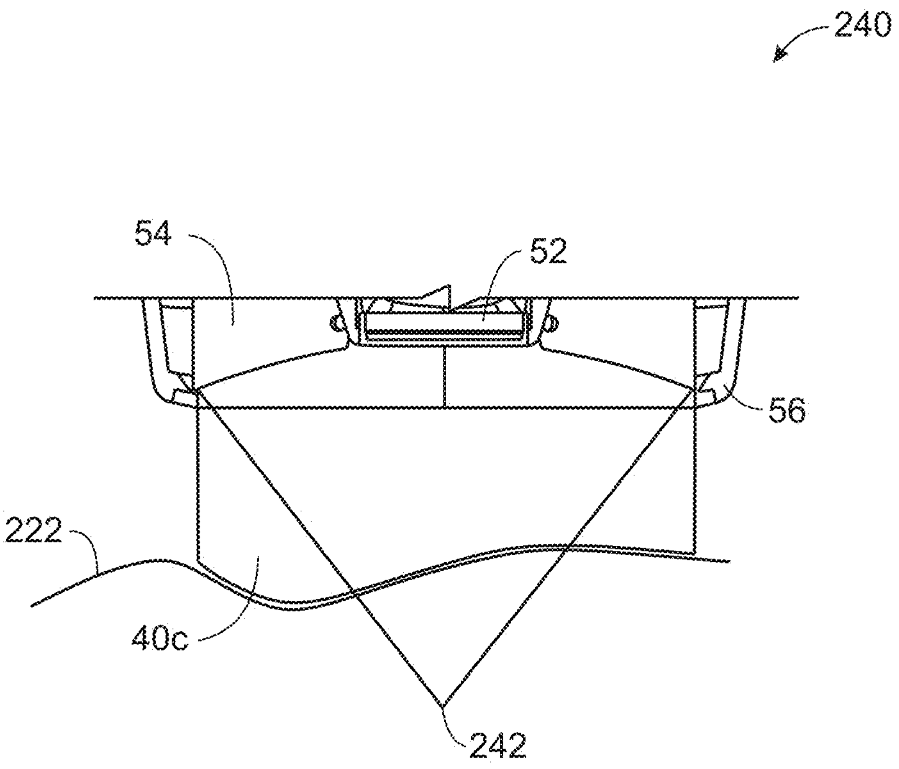
FIG. 15 is a schematic of a custom-molded gel standoff for a patient, according to embodiments of the present disclosure.

By way of further example, FIG. 15 is a schematic 240 of a custom-molded gel standoff 40*c* for a patient. In general, the schematic 240 includes the custom-molded gel standoff 40, wherein the custom-molded gel standoff 40 was designed to conform to the patient profile. For example, the gel standoff 40*c* may be customized when the determined probe placement position for a patient has an above average degree of patient skin 222 surface contour which may make it challenging to maintain contact with the skin surface 222. In this way, the gel standoff 40*c* may conform to the patient's skin 222 at the ultrasound probe placement location, thereby enabling delivery of an ultrasound therapy beam towards a target anatomy 242.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A gel standoff, comprising:

a gel standoff body comprising a moldable material;

one or more mating features formed within the gel standoff body, wherein the one or more mating features comprise one or more grooves configured to engage with one or more corresponding ridges formed within an internal cavity of an ultrasound probe so as to secure the gel standoff to the ultrasound probe and disengage with the one or more corresponding ridges so as to release the gel standoff from the ultrasound probe; and a skin-facing surface, wherein the skin-facing surface is configured to contact a subject's skin when in use.

2. The gel standoff of claim 1, wherein the moldable material comprises a hydrogel.

3. The gel standoff of claim 1, wherein the moldable material comprises a phase changing material.

4. The gel standoff of claim 3, wherein the phase changing material changes phase at least partly in response to a temperature of the phase changing material reaching or exceeding a melting point threshold.

5. The gel standoff of claim 4, wherein the phase changing material exhibits a melting temperature ranging from about 30° C. to about 40° C.

6. The gel standoff of claim 1, wherein the moldable material comprises a plasticized elastomeric polymer.

7. The gel standoff of claim 1 comprising a multi-layered material.

8. The gel standoff of claim 1, wherein the moldable material conforms to a patient profile based on a depth of a region of interest so as to pre-angulate an ultrasound probe in a certain direction when in use, or a combination thereof.

9. The gel standoff of claim 1, wherein the one or more mating features comprise one or more of a snap fit, interference fit, cantilever fit, annular fit, or torsional fit alone or in combination with one another.

10. The gel standoff of claim 1, wherein the one or more mating features are configured to reversibly mate with one or more complementary structural features of the ultrasound probe.

11. The gel standoff of claim 3, wherein the phase changing material changes phase at least partly in response to acoustic energy.

12. The gel standoff of claim 1, wherein the gel standoff body comprises a self-wetting material.

13. The gel standoff of claim 1, wherein the gel standoff is packaged into a container comprising a wetting fluid.

14. A method of mounting a gel standoff to an ultrasound probe comprising the steps of: opening a gel pad pack, wherein the gel standoff is exposed in the gel pad pack when opened; aligning the gel pad pack with an ultrasound probe, wherein one or more mating features of the gel standoff are aligned with complementary mating features of the ultrasound probe when aligned; contacting the gel standoff in the gel pad pack with the ultrasound probe, wherein the gel standoff engages with the ultrasound probe in response to the contact; and separating the ultrasound probe with the engaged gel standoff from the gel pad pack; wherein the gel standoff comprises: a gel standoff body comprising a moldable material;

one or more mating features formed within the gel standoff body, wherein the one or more mating features comprise one or more grooves configured to engage with one or more corresponding ridges formed within an internal cavity are configured to conform to one or more structural features of an ultrasound probe so as to secure the gel standoff to the ultrasound probe and disengage with the one or more corresponding ridges so as to release the gel standoff from the ultrasound probe; and a skin-facing surface, wherein the skin-facing surface is configured to contact a subject's skin when in use.

15. The method of claim 14, wherein the one or more mating features of the gel standoff comprise at least a snap and interference fit structural feature.

16. The method of claim 14, wherein the mating features of the ultrasound are integrated into a profile of the ultrasound probe.

17. The method of claim 14, wherein each mating feature of the mating features of the ultrasound probe is configured to couple to a complementary mating feature of the gel standoff.

18. The method of claim 14, wherein the gel standoff is configured to allow acoustic energy generated by the ultrasound probe to pass through.

19. A method of using a gel standoff comprising the steps of: inserting the gel standoff into a complementary cavity of an ultrasound probe; pressing the ultrasound probe against a subject; applying energy through the gel standoff toward a region of interest in the subject to cause neuromodulation; and removing the gel standoff from the ultrasound probe after the energy application is complete; wherein the gel standoff comprises: a gel standoff body comprising a moldable material;

one or more mating features formed within the gel standoff body, wherein the one or more mating features comprise one or more grooves configured to engage with one or more corresponding ridges formed within an internal cavity are configured to conform to one or more structural features of an ultrasound probe so as to secure the gel standoff to the ultrasound probe and disengage with the one or more corresponding ridges so as to release the gel standoff from the ultrasound probe; and a skin-facing surface, wherein the skin-facing surface is configured to contact a subject's skin when in use.

20. The gel standoff of claim 1, wherein the gel standoff body comprises angle-like features configured to cause the ultrasound probe to be angled relative to the subject's skin when applied.

21. The gel standoff of claim 20, wherein the moldable material is thicker on a first side of the gel standoff body relative to a second side of the gel standoff body so as to form the angle-like features.

* * * * *